(12) United States Patent
Gustavson et al.

(10) Patent No.: US 10,926,080 B2
(45) Date of Patent: Feb. 23, 2021

(54) WEARABLE CARDIOVERTER DEFIBRILLATOR WITH BREAST SUPPORT

(71) Applicant: West Affum Holdings Corp., Grand Cayman (KY)

(72) Inventors: Laura Marie Gustavson, Redmond, WA (US); Kerstin Dorst, Brooklyn, NY (US); Angela M. Stewart, Granite Falls, WA (US); Pamela Breske, New Castle, WA (US); Amanda K. Hall, Seattle, WA (US); Garrett McCann Kotlarchik, Kenmore, WA (US); Dallas Eugene Meeker, Kirkland, WA (US); Daniel James Finney, Woodinville, WA (US); Eduard Deml, Waldmuenchen (DE); Robert Reuben Buchanan, Bothell, WA (US); David Peter Finch, Bothell, WA (US); Phillip Dewey Foshee, Woodinville, WA (US); Douglas Keith Medema, Everett, WA (US); Kenneth F. Cowan, Kirkland, WA (US)

(73) Assignee: West Affum Holdings Corp., Grand Cayman (KY)

( * ) Notice: Subject to any disclaimer, the term of this patent is extended or adjusted under 35 U.S.C. 154(b) by 0 days.

(21) Appl. No.: 15/889,040

(22) Filed: Feb. 5, 2018

(65) Prior Publication Data

US 2018/0221648 A1 Aug. 9, 2018
US 2019/0134379 A9 May 9, 2019

Related U.S. Application Data

(60) Provisional application No. 62/443,686, filed on Jan. 7, 2017, provisional application No. 62/454,784, filed
(Continued)

(51) Int. Cl.
*A61N 1/04* (2006.01)
*A61N 1/39* (2006.01)
(Continued)

(52) U.S. Cl.
CPC .......... *A61N 1/0484* (2013.01); *A41C 3/0064* (2013.01); *A41D 1/005* (2013.01);
(Continued)

(58) Field of Classification Search
CPC .. A61N 1/3968; A61N 1/0484; A61N 1/3904; A61N 1/046; A41C 3/0064;
(Continued)

(56) References Cited

U.S. PATENT DOCUMENTS 3,724,355 A   4/1973   Unger
3,724,455 A   4/1973   Unger
(Continued)

FOREIGN PATENT DOCUMENTS

DE   2005060985 A1   6/2007
EP       2305110 B1   4/2018
(Continued)

OTHER PUBLICATIONS

Klein, Helmut U. et al., Risk Stratification for Implantable Cardioverter Defibrillator Therapy: The Role of the Wearable Cardioverter-Defibrillator, Clinical Update, European Heart Journal, May 31, 2013, 14 pages, European Society of Cardiology, France.
(Continued)

*Primary Examiner* — Paula J Stice
(74) *Attorney, Agent, or Firm* — Christensen O'Connor Johnson Kindness PLLC

(57) ABSTRACT

A supportive clothing article for a wearable cardioverter defibrillator (WCD), including a belt, the belt including a first end with a first portion of a fastener and a second end with a second portion of the fastener, wherein the belt is
(Continued)

structured to fasten around the torso of patient below the chest area of the patient, the belt including a first conductive mesh portion adjacent the first end of the belt or the second end of the belt, two straps, a back portion extending from the belt at an intermediary position on the belt to each of the two straps, the back portion including a conductive mesh, a first support receptacle attached to and extending from the belt and attachable to one of the two straps, and a second support receptacle attached to and extending from the belt and attachable to the other of the two straps.

27 Claims, 13 Drawing Sheets

Related U.S. Application Data on Feb. 4, 2017, provisional application No. 62/556,693, filed on Sep. 11, 2017.

(51) Int. Cl.
  *A41C 3/00* (2006.01)
  *A41D 1/00* (2018.01)

(52) U.S. Cl.
  CPC ........... *A61N 1/046* (2013.01); *A61N 1/3904* (2017.08); *A61N 1/3968* (2013.01); *A41D 2300/32* (2013.01); *A41D 2300/324* (2013.01); *A41D 2300/326* (2013.01)

(58) Field of Classification Search
  CPC ...... A41C 3/00; A41D 1/005; A41D 2300/32; A41D 2300/324; A41D 2300/326
  See application file for complete search history.

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Hellman et al. |
| 5,228,449 A | 7/1993 | Christ et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lysler |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Moth et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,560,044 B2 | 10/2013 | Kurzweil et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,897,860 B2 | 11/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,345,898 B2 | 5/2016 | Piha et al. |
| 9,408,548 B2 | 8/2016 | Volpe et al. |
| 9,445,719 B2 | 9/2016 | Libbus et al. |
| 9,579,020 B2 | 2/2017 | Libbus et al. |
| 9,591,983 B2 | 3/2017 | Amir et al. |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0302860 A1 | 11/2012 | Volpe et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0324112 A1 | 10/2014 | Macho et al. |
| 2014/0378812 A1 | 12/2014 | Saroka et al. |
| 2015/0039053 A1 | 2/2015 | Kaib |
| 2015/0297135 A1 | 10/2015 | Shoshani et al. |
| 2016/0004831 A1 | 1/2016 | Carlson et al. |

(56) References Cited

U.S. PATENT DOCUMENTS

| | | |
|---|---|---|
| 2016/0076175 A1 | 3/2016 | Rock |
| 2016/0076176 A1 | 3/2016 | Rock |
| 2016/0113581 A1 | 4/2016 | Amir et al. |
| 2016/0256104 A1 | 9/2016 | Romem et al. |
| 2016/0271384 A1* | 9/2016 | Kaib .................. A61N 1/0492 |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0319862 A1 | 11/2017 | Foshee, Jr. et al. |
| 2017/0332718 A1* | 11/2017 | Eyal .................. A41C 3/0028 |
| 2017/0367591 A1 | 12/2017 | Jorgenseon |
| 2018/0116537 A1 | 5/2018 | Sullivan et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |
| 2020/0155826 A1 | 5/2020 | Kaib et al. |

FOREIGN PATENT DOCUMENTS

| | | |
|---|---|---|
| JP | 4320257 B2 | 8/2009 |
| JP | 2014526282 A | 10/2014 |
| JP | 5963767 B2 | 8/2016 |
| WO | 1998039061 A2 | 9/1998 |
| WO | 2011146448 A1 | 11/2011 |
| WO | 2012064604 A1 | 5/2012 |
| WO | 2012151160 A1 | 11/2012 |
| WO | 2015056262 A1 | 4/2015 |

OTHER PUBLICATIONS

Lifecor LifeVest System Model WCD 3100 Operator's Manual, 2006, ZOLL Lifecor Corporation, Pittsburgh, PA, PN 20B0040 Rev FI, 48 pages.

LifeVest Model 4000 Patient Manual, 108 pages, ZOLL, Pittsburgh, PA, PN 20B0047 Rev B.

Heartstart MRx and XL AED Algorithm—Application Note, Jul. 2001, Edition 2, Philips Healthcare, USA.

The LifeVest Network/Patient Data Management System, Zoll, 2015, 20C0503 Rev A.

Zoll, LifeVest, Proven protection from Sudden Cardiac Death, dated Mar. 27, 2018, 4 pages. Pittsburgh PA, USA.

LifeVest, System Model WCD 3100, Life Cor Operators manual, dated Mar. 27, 2018, 48 pages. ZOLL Lifecor corporation, Pittsburgh PA, USA.

LifeVest, Model 4000, Patient Manual, dated Mar. 27, 2018, 108 pages. ZOLL, Pittsburgh PA, USA.

HeartStart, AED Algorith, Application note, Published Jul. 2011, 10 pages. Edition 2, Philips Healthcare, Andover MA, USA.

Klein, Risk stratification for implantable cardioverter defibrillator therapy. Clinical update, Published May 31, 2014, 14 pages. ZOO, Pittsburgh PA, USA.

International Search Report and Written Opinion for PCT Application No. PCT/US2015/051726, dated May 20, 2016, European Patent Office, Rijswijk, 11 pages.

* cited by examiner

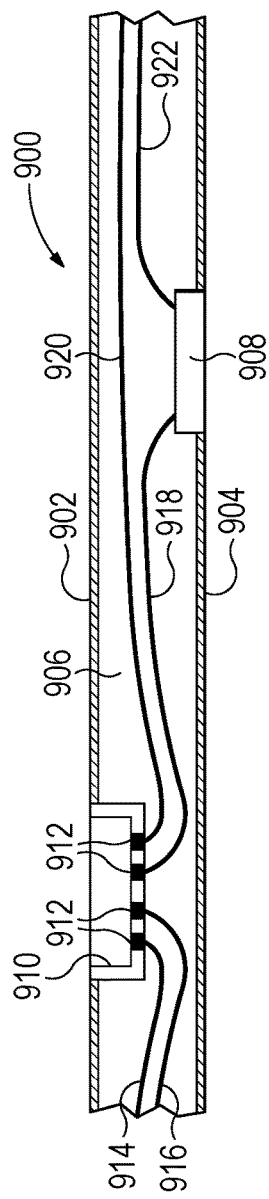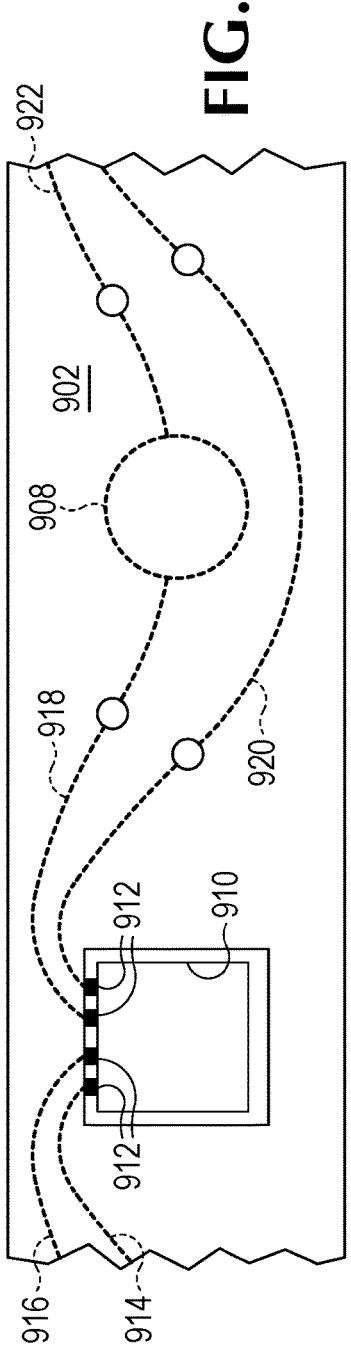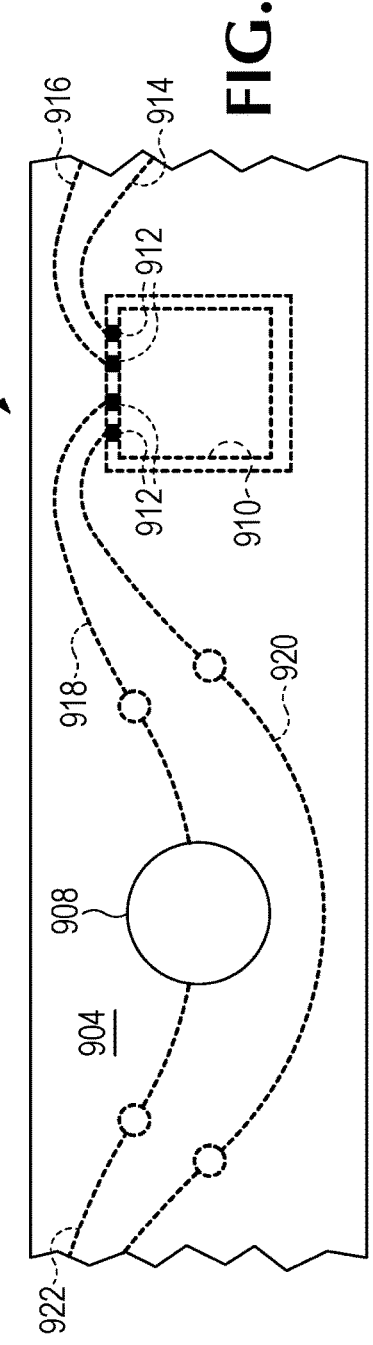

WEARABLE CARDIOVERTER DEFIBRILLATOR WITH BREAST SUPPORT

This application claims priority from U.S. Provisional Patent Application No. 62/454,784, filed Feb. 4, 2017, entitled "WCD GARMENT SUBTLETIES," and claims priority from U.S. Provisional Patent Application No. 62/556,693, filed Sep. 11, 2017, entitled "WEARABLE MEDICAL SYSTEM ASSEMBLY."

BACKGROUND

Sudden cardiac arrest accounts for more than 300,000 deaths in the United States alone, annually. Some of the high-risk population, such as post-myocardial infarction patients, that have implantable cardioverter defibrillators (ICD) have been shown in randomize trials to have a reduced mortality rate from those in the high-risk population that do not have ICDs.

However, there exists a population of patients who are not deemed appropriate candidates for ICDs for a variety of reasons but may still benefit from automatic external defibrillation. A wearable cardioverter defibrillator (WCD) is a device designed for patients at risk of sudden cardiac death (SCD) who are not immediate candidates for ICD therapy. The WCD is an external device including a fabric garment assembly that is fitted onto a patient's chest which holds electrodes in place and is capable of automatic detection and defibrillation of ventricular tachycardia (VT) or ventricular fibrillation (VF).

However, WCDs conventionally have been designed as unisex devices that may not be comfortable for a female patient's anatomy. Conventional WCDs generally required a female patient to either wear a bra over the WCD, which may result in discomfort, or forego a bra, which may lead to lack of support of the breasts of the female patient. Further, conventional WCDs often have loose wires that can get tangled in a patient's clothing and be uncomfortable for the patient.

This disclosure addresses these and other deficiencies of the prior art.

BRIEF DESCRIPTION OF THE DRAWINGS

Aspects, features and advantages of embodiments of the present disclosure will become apparent from the following description of embodiments in reference to the appended drawings in which:

FIG. 9 illustrates a cross section of a double layer construction of a supportive clothing article according to some embodiments of the disclosure.

FIG. 10 illustrates an outer layer of the double layer construction of FIG. 9.

FIG. 11 illustrates an inner layer of the double layer construction of FIG. 9.

DESCRIPTION

In general, embodiments of the disclosure relate to a wearable cardioverter defibrillator (WCD) including a supportive clothing article for including a belt, the belt including a first end with a first portion of a fastener and a second end with a second portion of the fastener, wherein the belt is structured to fasten around the torso of patient below the chest area of the patient, the belt including a first conductive mesh portion adjacent the first end of the belt or the second end of the belt, two straps, a back portion extending from the belt at an intermediary position on the belt to each of the two straps, the back portion including a conductive mesh, a first support receptacle attached to and extending from the belt and attachable to one of the two straps, and a second support receptacle attached to and extending from the belt and attachable to the other of the two straps.

Embodiments of the disclosure also relate to a wearable cardioverter defibrillator (WCD) including a supportive clothing article including a belt, having a two fabric layers construction, including a first side with a first portion of a fastener and a second side with a second portion of the fastener, wherein the belt is structured to fasten around the torso of patient below the chest area of the patient, the belt including a first conductive mesh portion on the inner layer adjacent the first side of the belt or the second side of the belt, two adjustable straps, a back portion, having a two fabric layer construction, extending from the belt at an intermediary position on the belt to each of the two straps, an inner layer of the back portion including a conductive mesh, and polyurethane tape attached to an end of the belt.

Embodiments of the disclosure also relate to a wearable cardioverter defibrillator (WCD) including a supportive clothing device having a supportive clothing article including a patient facing fabric layer, an outer fabric layer, an interior defined by the patient facing fabric layer and the outer fabric layer, the interior including, at least one electrical component, and a plurality of wires, at least one wire connected to the at least one electrical component.

Figure 1:
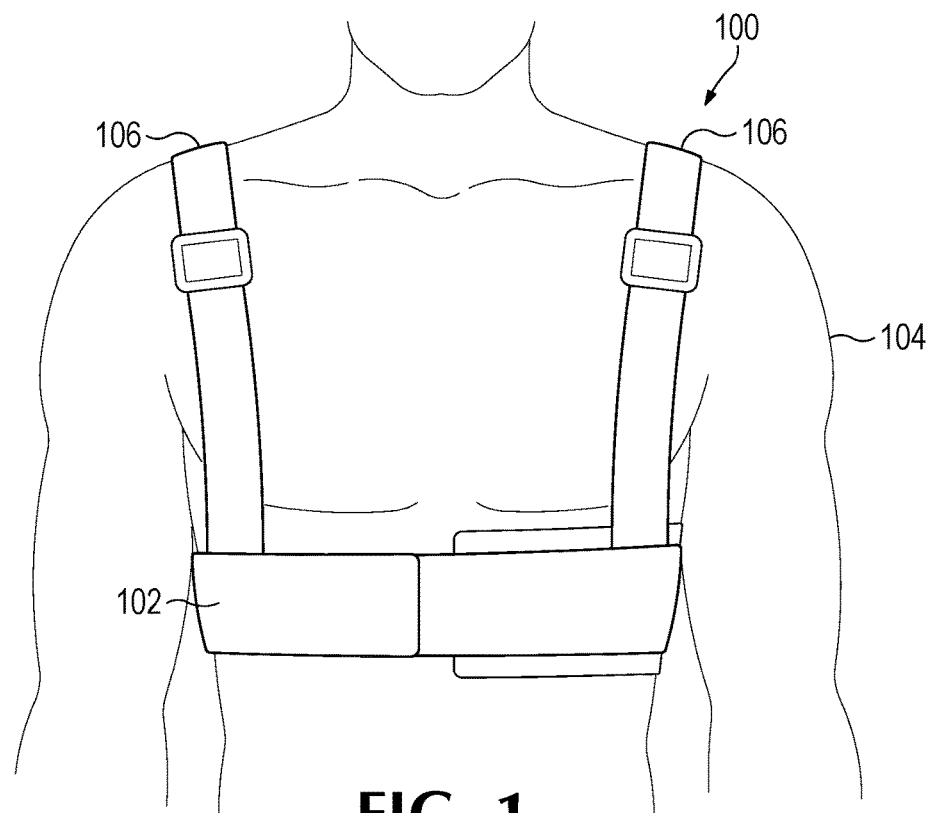
FIG. 1 illustrates a conventional WCD worn by a patient.

FIG. 1 illustrates a conventional WCD 100 having a belt 102 structured to wrap around a torso of a patient 104 below a chest area. The WCD 100 also includes two adjustable straps 106. The conventional WCD 100 is illustrated on a male patient 104.

The straps 106 of the convention WCD 100 often cut into the outer edge of the breasts of a female patient. Further, a female patient either must wear a bra to support the breasts over the conventional WCD 100, often a larger size bra than normal, or go without a bra. Female patients are often also unable to wear a preferred type of bra, such as an underwire bra, and the physical interference between the bra and the conventional WCD 100 can cause discomfort, such as pinching, to the female patient. The belt 102 of the conventional WCD 100 often rides up and cuts into the breast fold at the chest area of the female patient.

Figure 2:
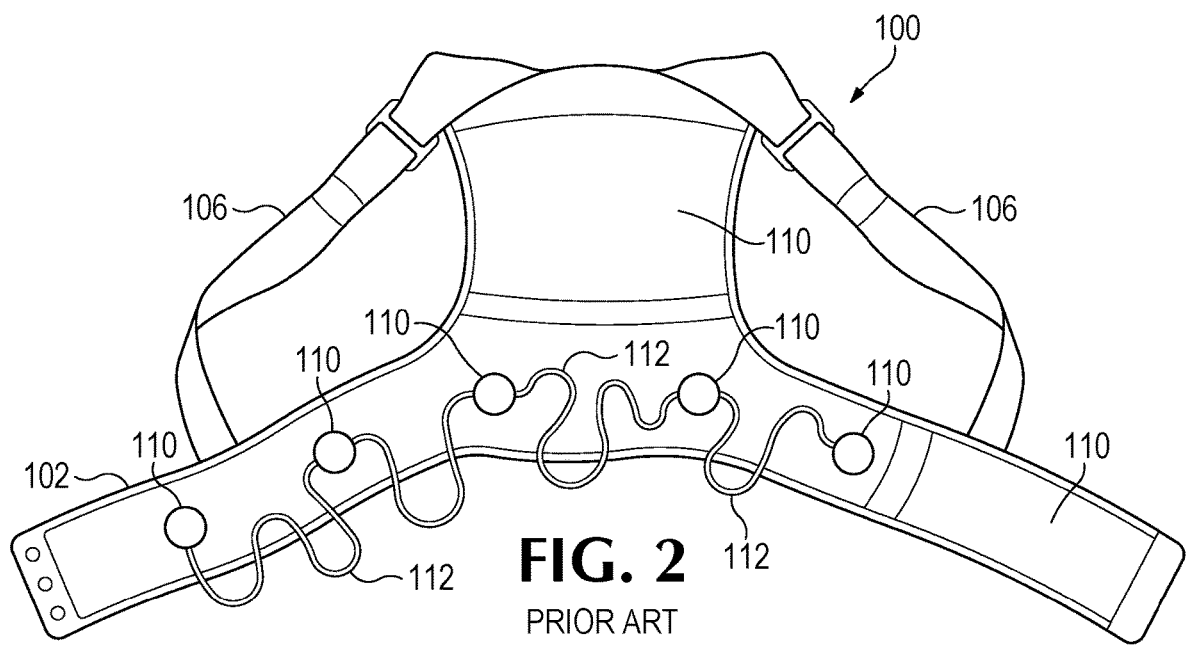
FIG. 2 illustrates the conventional WCD of FIG. 1 not worn by a patient.

FIG. 2 illustrates further components of the conventional WCD 100 when not worn by the patient 104. The conventional WCD 100 may include a back portion 108 that extends from the belt 102 to the straps 106. The conventional WCD 100 may also include a number of electrodes 110 along the belt 102 and the back portion 108. The electrodes 110 may be used to determine an electrocardiogram (ECG) of a patient and/or to provide defibrillation to the patient. To connect the electrodes 110 to an electronic module for defibrillation, loose wires 112 are used to connect the various electrodes and other electrical components. The loose wires 112 often get tangled and can be pulled on when a patient 104 is getting dressed or undressed, which may injure a patient 104 or may damage the electrodes or other various electrical components attached to the wires 112.

Figure 3:
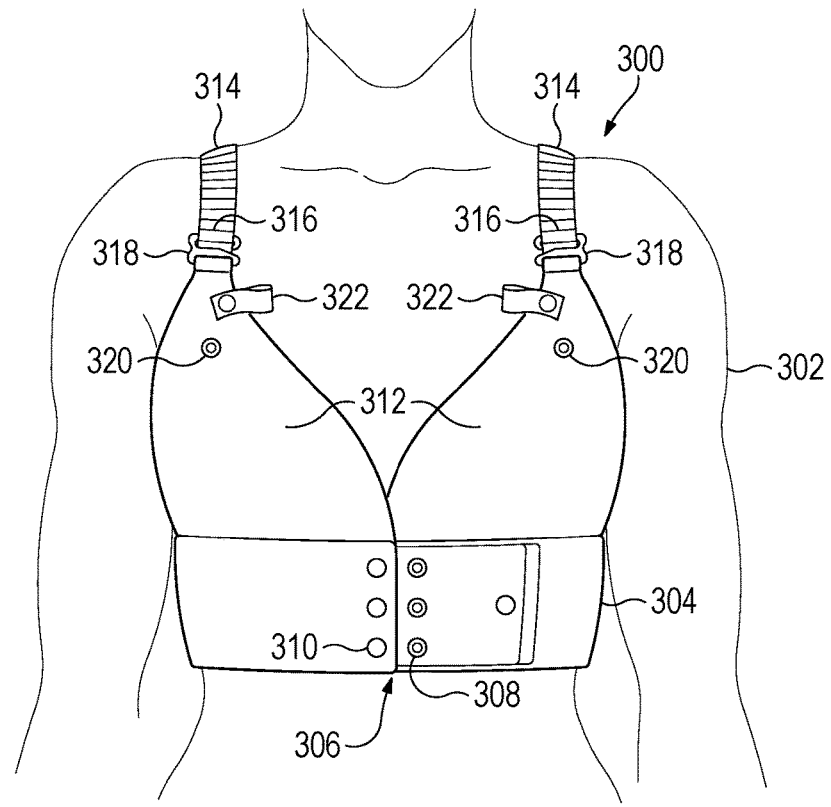
FIG. 3 illustrates a supportive clothing article for a WCD worn by a patient according to some embodiments of the disclosure.
Figure 4:
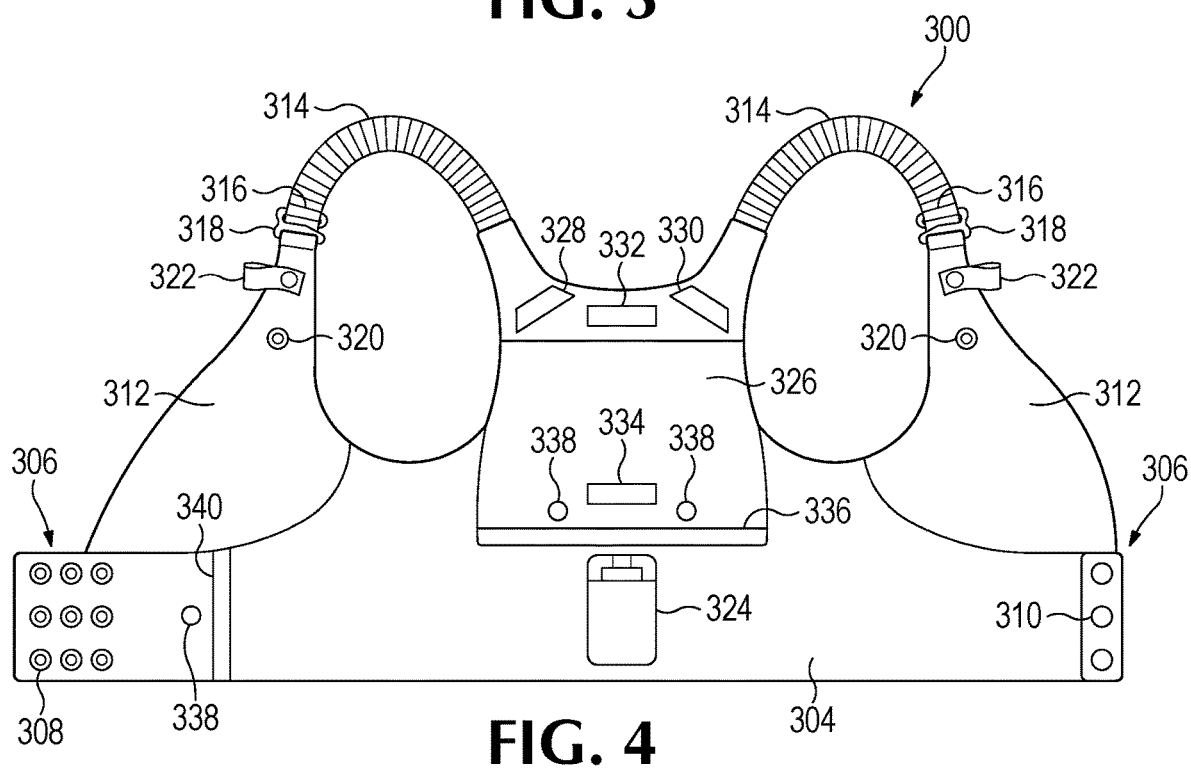
FIG. 4 illustrates the supportive clothing article of FIG. 3 not worn by a patient.

FIGS. 3 and 4 illustrates a WCD supportive clothing article 300 according to some embodiments of the disclosure. FIG. 3 illustrates the supportive clothing article 300 on a female patient 302, while FIG. 4 illustrates an outer layer of the supportive clothing article 300 laying flat when not worn by a patient. While the supportive clothing article 300 is shown on a female patient, the supportive clothing article 300 may be worn by a patient of any gender, particularly a patient who prefers breast support.

The supportive clothing article 300 includes an integrated belt 304 structured to wrap around a torso of the patient 302 below a chest area. The belt 304 may include a fastener, such as a snap fastener 306. Although a snap fastener 306 is shown in FIG. 3, any type of suitable fastener may be used, such as a hook and eye fastener, a hook and loop fastener, or a button fastener, for example. As illustrated in FIG. 4, the snap fastener 306 may include a number of male components 308 arranged in a number of rows. The side of the belt 304 with the male components 308 of the snap fastener is longer than the side of the belt 304 with female components 310 in a single row. That is, the belt 304 may be adjustable in size around the torso of the patient 302. In some embodiments, three rows of male components 308 are provided and a first breast support receptacle 312, discussed in more detail below, starts at the second row of male components 308 and a second breast support receptacle 312 starts at the single row of female components 310.

The first and second breast support receptacles 312 start at the belt 304 and extend upwards, each toward a respective adjustable strap 314. The adjustable straps 314 may include ultrasonic bonded straps that have a number of loops 316 structured to receive hooks 318 located at the top of the breast support receptacles 312. The straps 314 are adjustable by selecting the desired loop 316 in the strap 314 to connect the hook 318. The lower the loop 316 used, the longer the strap 314 will be on the patient 302. While bonded loop shoulder straps 314 are shown, one of ordinary skill in the art will readily understand that other types of adjustable or non-adjustable (such as elastic) straps may be used. For example, a tri-glide strap may be used in the front of device, instead of the bonded loops and hooks.

Each breast support receptacle 312 may have a generally triangular shape, as shown in FIGS. 3 and 4. The breast support receptacles 312 are constructed of one or more layers of a thin, stretchable fabric. In some embodiments, the fabric is a wicking fabric.

Snaps 320 may be located on one or both of the breast support receptacles 312. The snaps 320 are structured to mate with a matching snap located on a user device that connects to the defibrillator, such as an alert button. The supportive clothing article 300 may also include one or more flaps 322 that hold the cable(s) for the user device in place. The flaps 322, for example, may snap to the breast support receptacles 312 so that they may be opened to insert the cord(s) and then closed to hold the cord(s) in place. In other embodiments, the flaps 322 may be connected via a button or a hook and loop fastener, or the flaps 322 may be elastic and extend to receive the user device and cords through the flaps 322.

As seen in FIG. 4, the supportive clothing article may include a receptacle 324 located on the belt 304. The receptacle 324 is structured to accept an electronic module that connects to the support clothing article 300 to receive inputs from and send instructions to various defibrillation components. The receptacle 324 may contain electrical contacts, as discussed in more detail below, to electrically connect various electrical components to the supportive clothing device that may be used by the defibrillator, such as electrodes and a control module, for example. In some embodiments, receptacle 324 may contain a hard plastic lining to receive the electronic module. In other embodiments, rather than a receptacle 324, another connector may be used to physically and electrically connect the electronic module to the supportive clothing article 300.

The supportive clothing article 300 also includes a back portion 326 structured to extend from the belt 304 to the straps 314. As seen in FIG. 4, the back portion 326 may extend into the belt 304. That is, the belt 304 includes a straight hem at a bottom portion of the belt 304, and a curved hem from the top portion of the belt, the top portion curving upwards from the snap fastener on each side. The belt 304 includes a portion that is located between the breast receptacle 312 and the back portion 326 on each side, in an area corresponding to an underarm area of the patient 302.

The back portion 326 may include cable guides 328, 330, 332, and 334, to align the cable(s) from the electronic module to the user device along the spine and the shoulders of the patient 302. The cable guides 328, 330, 332, and 334 may be elastic loops to keep the wires in place along the spine of the patient 302. In other embodiments, the cable guides 328, 330, 332, and 334 may be removable to add the cable, such as with a snap fastener, and then reattached over the cable. This keeps the cables routed over the spine instead of over the shoulder blades, which provides comfort to the patient 302 when seated. Because of the natural depression in the spine of the patient 302, the cables can more comfortably sit in this area. That is, the cable(s) may be secured between cable guides 332 and 334, and then may be secured around the shoulder of the patient 302 using either cable guide 328 or 330. Cable guides 328, 330, 332, and 334 may also be included in a male or unisex version of a supportive clothing article.

A pocket or opening 336 may be provided at the top of the belt 304 that abuts the back portion 326. The pocket or opening 336 may include a fastener 338 to close the pocket or opening 336. Further, a pocket or opening 340 may also be provided along the belt 304 near the male components 308 of the snap fastener 306, along with another fastener 338. The pockets and openings 336 and 340 may be used to place electrical components and/or wires within the supportive clothing article 300, which will be discussed in more detail below with reference to FIGS. 9-11.

Figure 5:
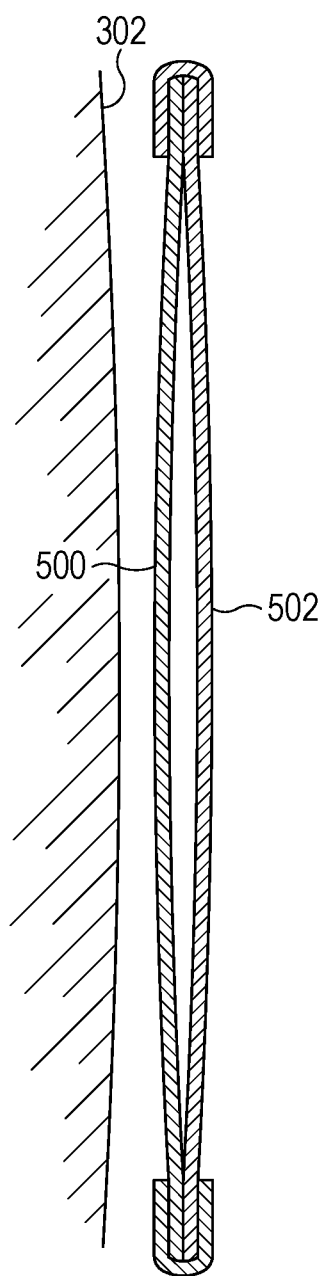
FIG. 5 illustrates a double layer construction of a supportive clothing article according to some embodiments.

In some embodiments, the supportive clothing article 300 may be constructed with a double fabric layer construction, as shown in FIG. 5. The supportive clothing article 300 may include an inner fabric layer 500 that faces a garment wearer 302, i.e., a patient, and an outer fabric layer 502 that faces away from the garment wearer 302. As mentioned above and will be discussed below with reference to FIGS. 9-11, this double fabric layer construction may allow for wires and other electrical components to be placed within the support clothing article 300 to prevent the wires from being tangled by the patient or bothersome to the patient. However, as discussed in more detail below, an inner fabric layer of a breast receptacle, for example, may be different from an inner fabric layer of a belt or a back portion.

Although not shown in FIGS. 3 and 4, the belt 304 may contain one or more electrodes either within, attached it, or on the inner fabric layer 500 that faces the garment wearer or patient 302. In some embodiments, the belt 304 may contain electrical contacts for the electrodes to connect, rather than the electrodes themselves. The electrodes may be used, for example, by the electronic module to determine an ECG of the patient.

Figure 6:
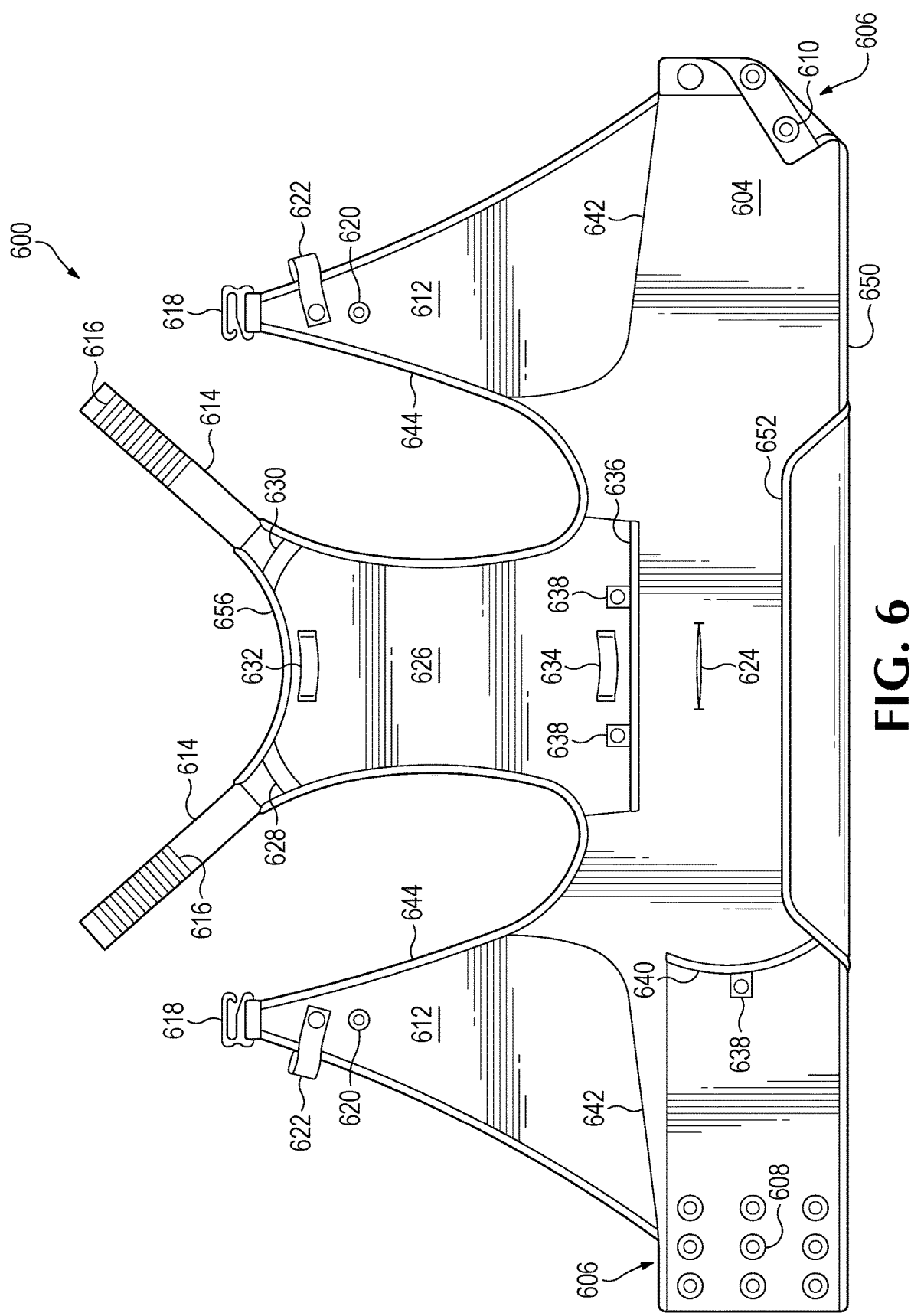
FIG. 6 illustrates an outer layer of a supportive clothing article for a WCD according to some embodiments of the disclosure.
Figure 7:
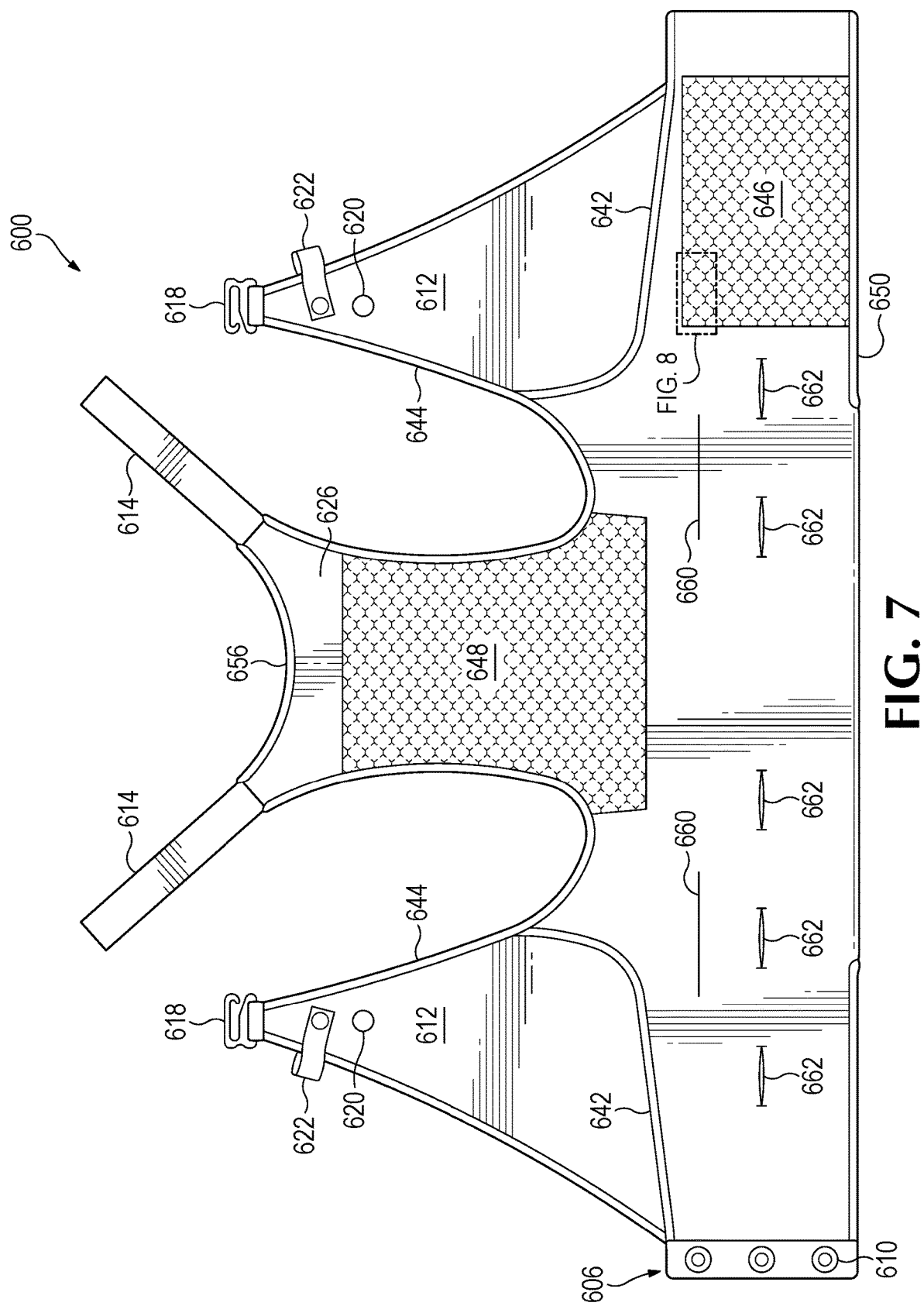
FIG. 7 illustrates an inner layer of a supportive clothing article for a WCD according to some embodiments of the disclosure.

FIGS. 6 and 7 illustrates another embodiment of a supportive clothing article 600 having a double fabric layer construction according to some embodiments of the disclosure. FIG. 6 illustrates an outer layer 502 while FIG. 7 illustrates an inner layer 500.

Similar to FIGS. 3 and 4, the supportive clothing article 600 may include an integrated belt 604 structured to wrap around a torso of a patient below a chest area. The belt may include a fastener 606, having a number of male components 608 and a number of female components 610, or any other type of fastener discussed above with respect to FIGS. 3 and 4 may be used. A first breast receptacle 612 may start at a middle row of the male components 608, and a second breast support receptacle 612 starts at the single row of female components 610.

Starting from the positions discussed above, the breast support receptacles 612 extend upward from the belt 604 toward a respective adjustable strap 614, having the loops 616 and hooks 618 discussed above, or any other alternative discussed above.

Snaps 620 may be located on one or both of the breast support receptacles 612. The snaps 620 are structured to mate with a matching snap located on a user device that connects to the defibrillator, such as an alert button. The supportive clothing article 600 may also include one or more flaps 622 that hold the cable(s) for the user device in place. The flaps 622, for example, may snap to the breast support receptacles 612 so that they may be opened to insert the cord(s) and then closed to hold the cord(s) in place. In other embodiments, the flaps 622 may be connected via a button or a hook and loop fastener, or the flaps 622 may be elastic and extend to receive the user device and cords through the flaps 622.

As seen in FIG. 4, the supportive clothing article 600 may include a receptacle 624 located on the belt 604. The receptacle 624 is structured to accept an electronic module that connects to the support clothing article 600 to receive inputs from and send instructions to various defibrillation components. The receptacle 624 may contain electrical contacts, as discussed in more detail below, to electrically connect various electrical components to the supportive clothing device that may be used by the defibrillator, such as electrodes and a control module, for example. In some embodiments, receptacle 624 may contain a hard plastic lining to receive the electronic module. In other embodiments, rather than a receptacle 624, another connector may be used to physically and electrically connect the electronic module to the supportive clothing article 600.

The supportive clothing article 600 also includes a back portion 626 structured to extend from the belt 604 to the straps 614. The back portion 626 may extend into the belt 604. That is, the belt 604 includes a straight hem at a bottom portion of the belt 604, and a curved hem from the top portion of the belt, the top portion curving upwards from the snap fastener on each side. The belt 604 includes a portion that is located between the breast receptacle 612 and the back portion 626 on each side, in an area corresponding to an underarm area of the patient 602.

Similar to FIGS. 3 and 4 discussed above, the back portion 626 may also include cable guides 628, 630, 632, and 634, to align the cable(s) from the electronic module to the user device along the spine and the shoulders of the patient 602. The cable guides 628, 630, 632, and 634 may be elastic loops to keep the wires in place along the spine of the patient 602. In other embodiments, the cable guides 628, 630, 632, and 634 may be removable to add the cable, such as with a snap fastener, and then reattached over the cable. Additional features of the cable guides 628, 630, 632, and 634 discussed above apply in this embodiment as well and are not further discussed in detail here.

A pocket or opening 636 may be provided at the top of the belt 604 that abuts the back portion 626. The pocket or opening 636 may include a fastener 638 to close the pocket or opening 636. Further, a pocket or opening 640 may also be provided along the belt 604 near the male components 608 of the snap fastener 606, along with another fastener 638. The pockets and openings 636 and 640 may be used to place electrical components and/or wires within the supportive clothing article 600, which will be discussed in more detail below with reference to FIGS. 9-11.

Both the inner layer 500 and the outer layer 502 of the breast support receptacles 612 are gathered at the bottom seam 642 near the belt 604. Each breast receptacle 612 may include an opening 644 structured to receive a bra cup insert (not shown), in various sizes, to provide additional support for the breasts of a female patient. That is, the opening 644 allows the bra cup insert to be placed between the inner fabric layer 500 and the outer fabric layer 502.

In some embodiments, both the inner layer 500 and the outer layer 520 are the same fabric, such as, for the entirety of the supportive clothing article 300 may be made of the same fabric or the entire outer layer may be made of the same fabric, such as a thin, soft, and stretchy fabric, such as Sensitive® Plus fabric, available from EUROJERSEY S.P.A. For example, using industry standard testing, the fabric should exhibit at least a 125% increase in width and a 105% increase in length when subjected to a 15 Newtons (N) force, and at least a 175% increase in width and a 120% increase in length when subjected to a 35 N force. In some embodiments, each fabric layer is a wicking fabric to keep the patient dry and comfortable.

In some embodiments, different components of the supportive clothing article 300 include different fabric types. For example, the belt 604 may include a first fabric on the outer layer 500 portion of the belt 604 that includes the male components 608 of the fastener 606 until the opening 640, that includes stretch recovery materials, such as Sensitive® Sculpt fabric, also available from EUROJERSEY S.P.A. For example, using industry standard testing, the fabric should exhibit at least a 110% increase in width and an 85% increase in length when subjected to a 15 Newtons (N) force, and at least a 160% increase in width and a 110% increase in length when subjected to a 35 N force. This portion of the belt 604 may also include a foam layer between the inner layer 500 and the outer layer 502. The remainder of the outer layer 502 of the belt 604 is constructed of the Sensitive® Plus fabric.

The inner layer 500 of the belt 604 may be constructed of the Sensitive® Sculpt fabric as well, as the high recovery aspect of this material provides pressure on the electrodes, discussed in more detail below, against the body of the patient. However, a portion of the inner layer 500, as seen in FIG. 7, may include a conductive mesh 646 that connects to an electronic module of the defibrillator to provide defibrillation to the patient.

The outer layer 502 of the back portion 626 may include the Sensitive® Sculpt fabric, to maintain pressure on a conductive mesh portion 648 provided on the inner layer 500 of the back portion 626. The remaining material at the top portion above the conductive mesh portion 648 may also be the Sensitive® Sculpt fabric to provide additional pressure to the conductive mesh portion 648. In some embodiments, a foam and/or spacer mesh may be added between the outer layer 502 and the conductive mesh 646 and 648 to further provide pressure to conductive mesh 646 and 648, as well as improve gel transmission, discussed below. The conductive meshes 646 and 648 may be any conductive mesh that acts as an electrode during a defibrillation procedure, as discussed below, such as the conductive mesh 800 shown in FIG. 8.

Figure 8:
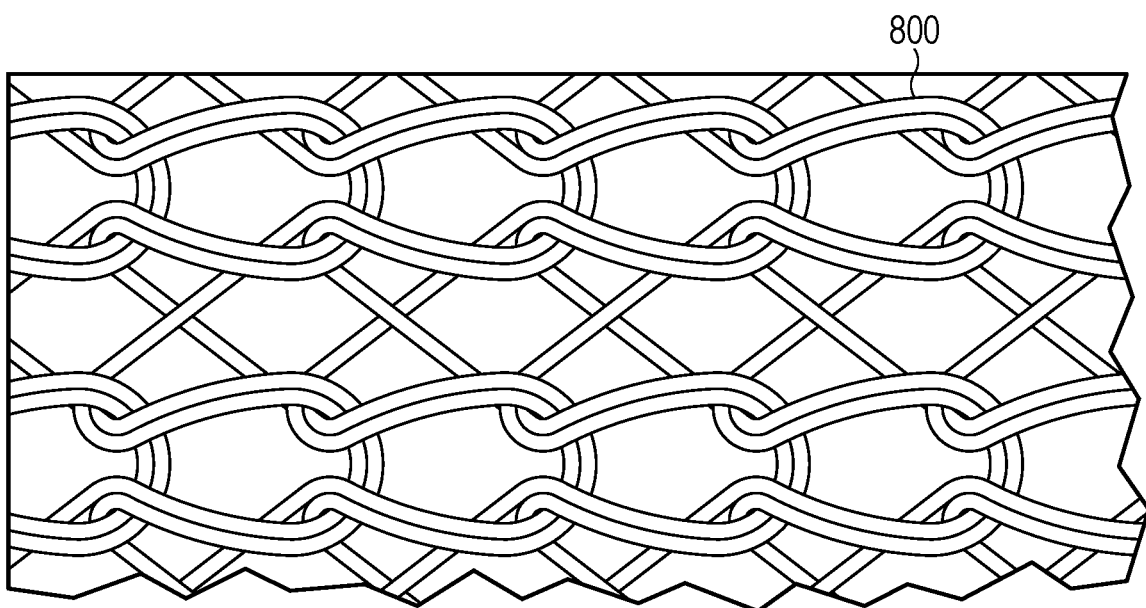
FIG. 8 illustrates an example conductive mesh according to some embodiments of the disclosure.
Figure 12:
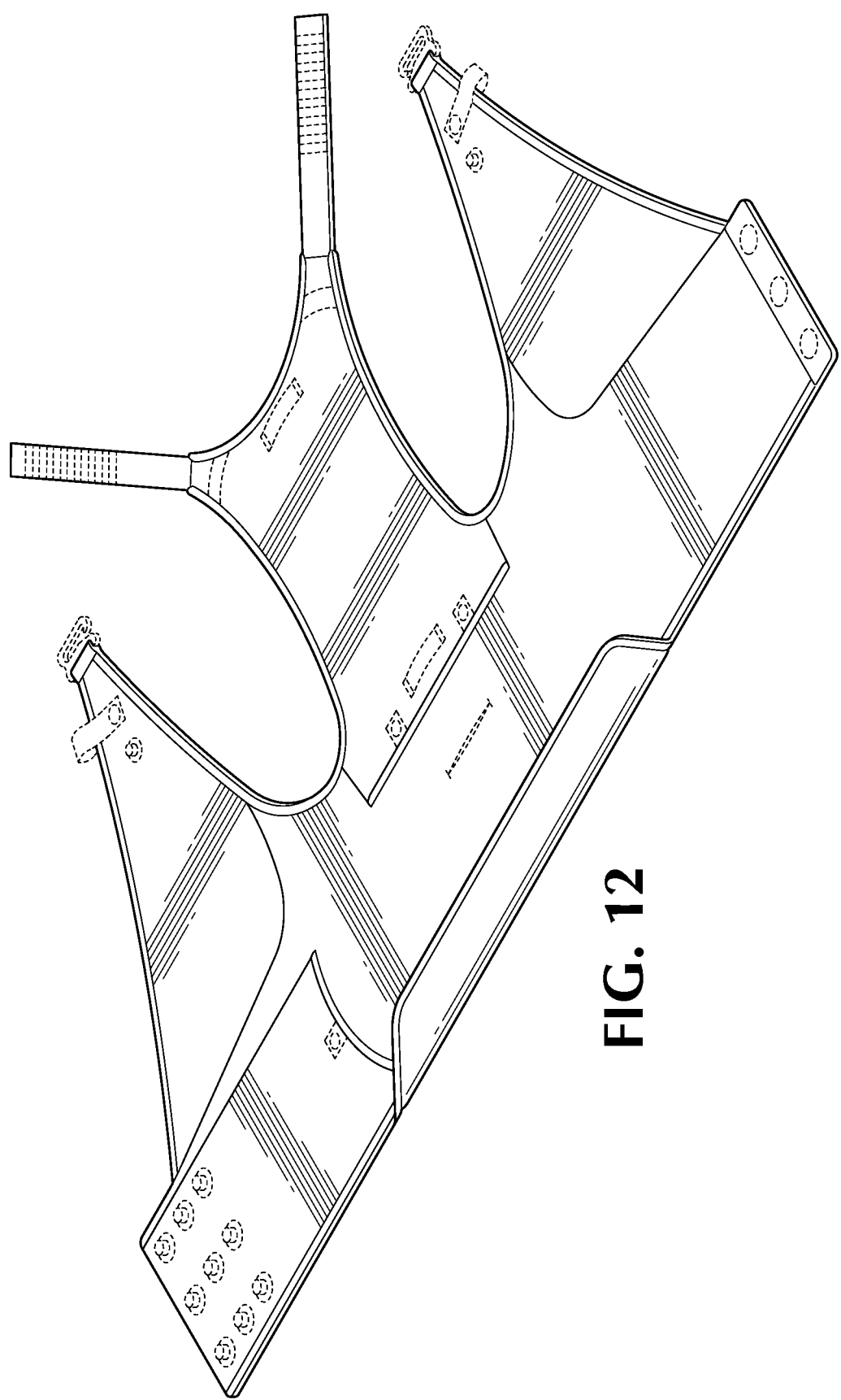
FIG. 12 illustrates the appearance of a rear, bottom perspective view of a supportive clothing article for a wearable cardioverter defibrillator in an embodiment.
Figure 13:
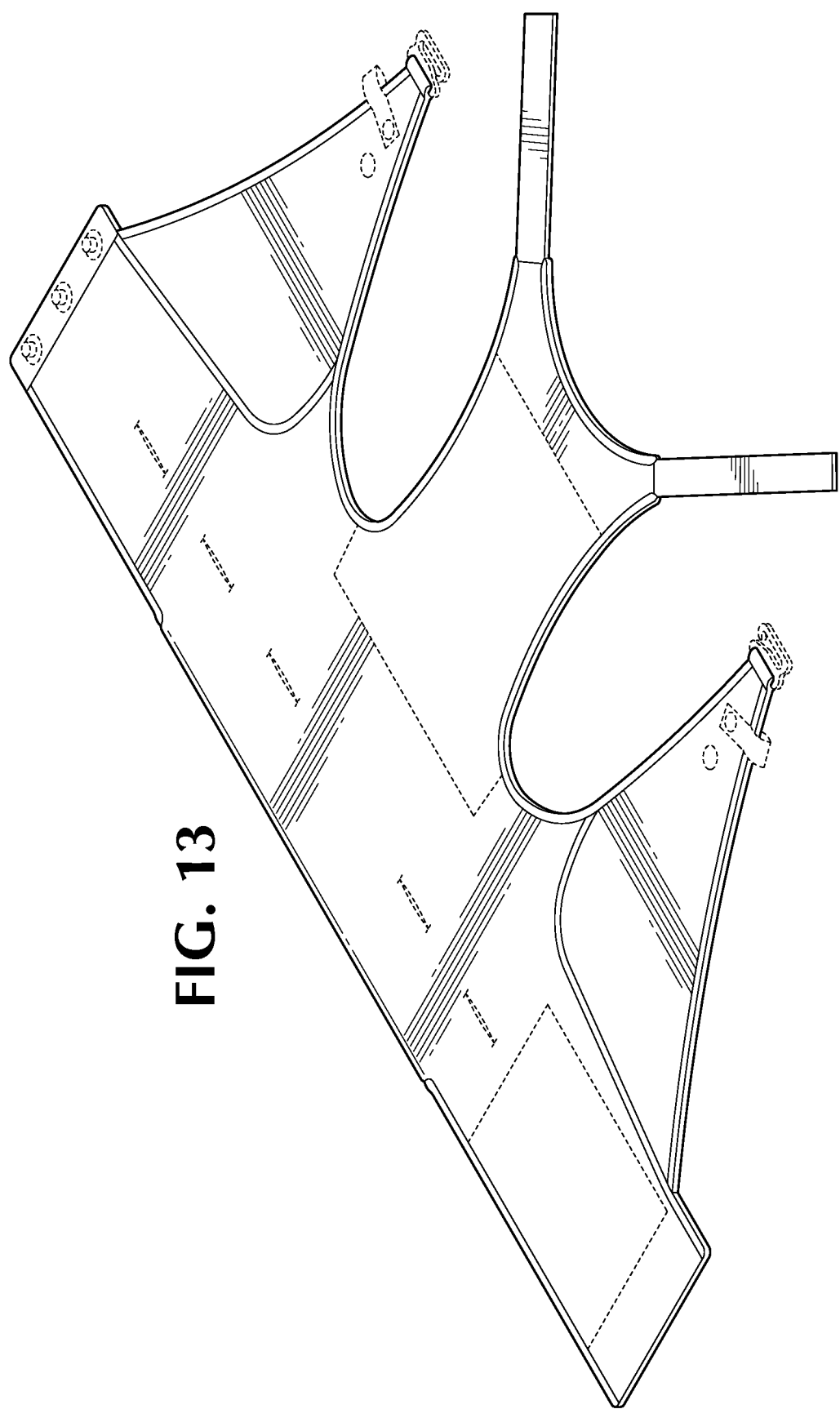
FIG. 13 illustrates the appearance of a front, bottom perspective view of the supportive clothing article of FIG. 12.
Figure 14:
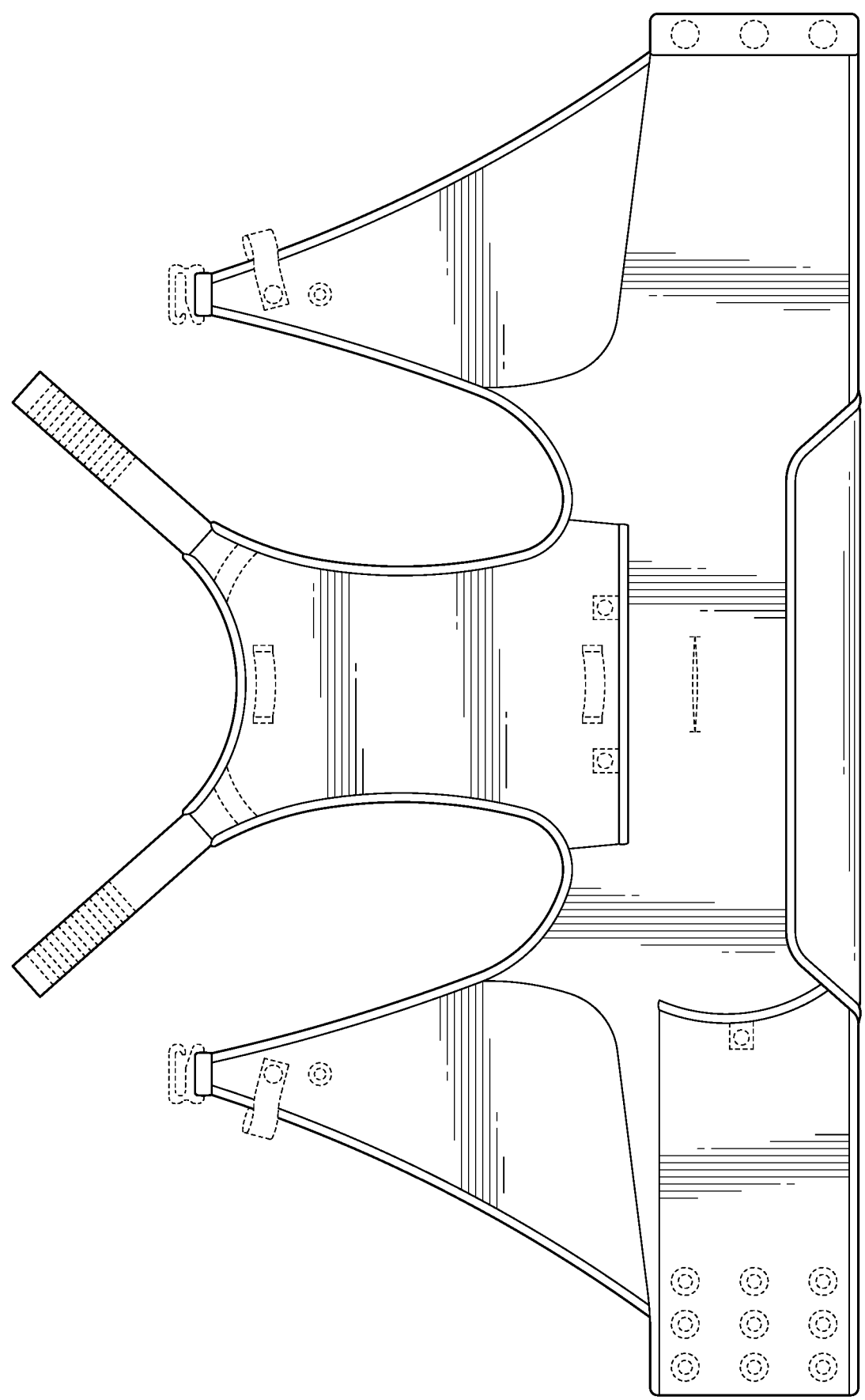
FIG. 14 illustrates the appearance of a rear view of the supportive clothing article of FIG. 12.
Figure 15:
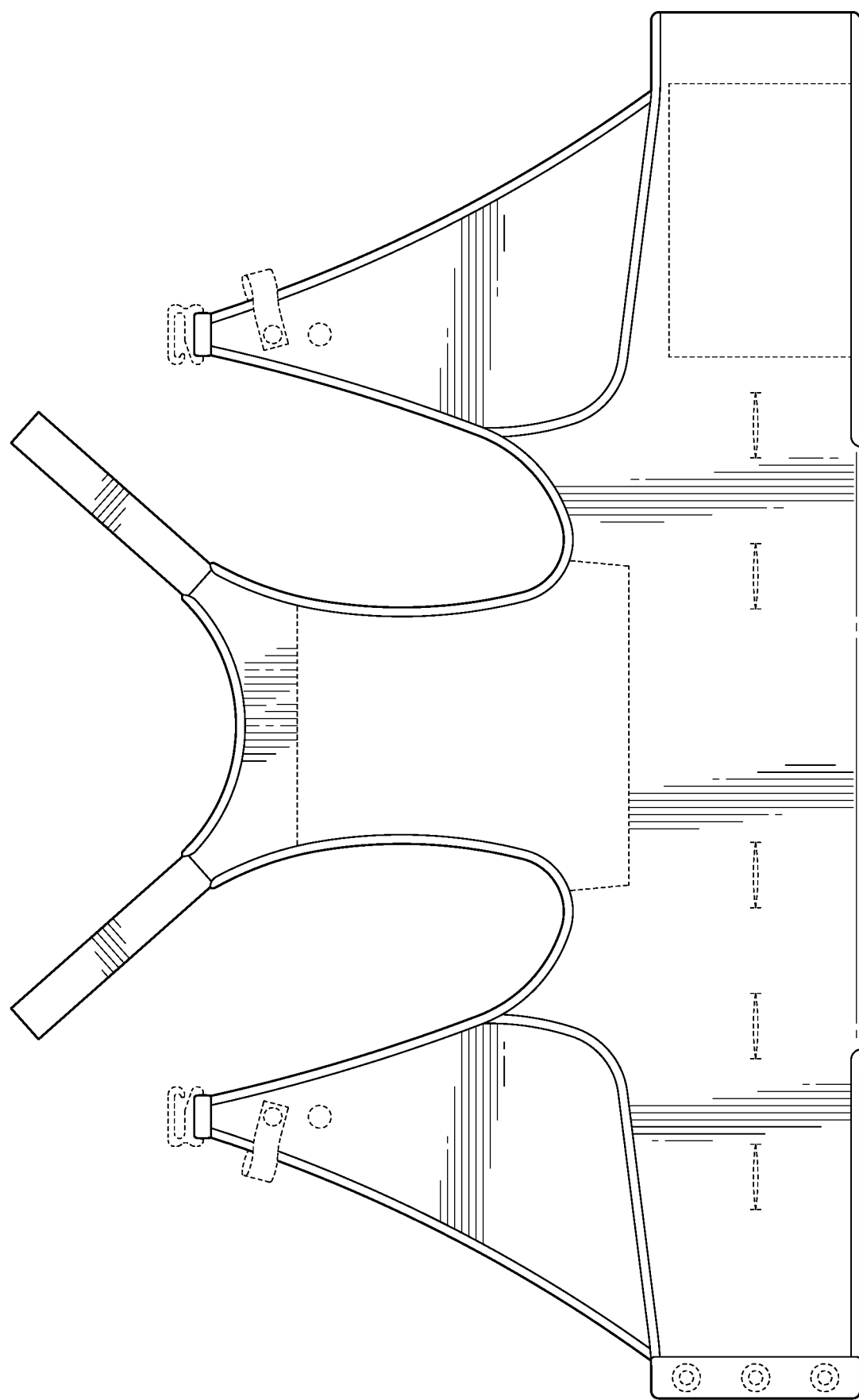
FIG. 15 illustrates the appearance of a front view of the supportive clothing article of FIG. 12.
Figure 16:
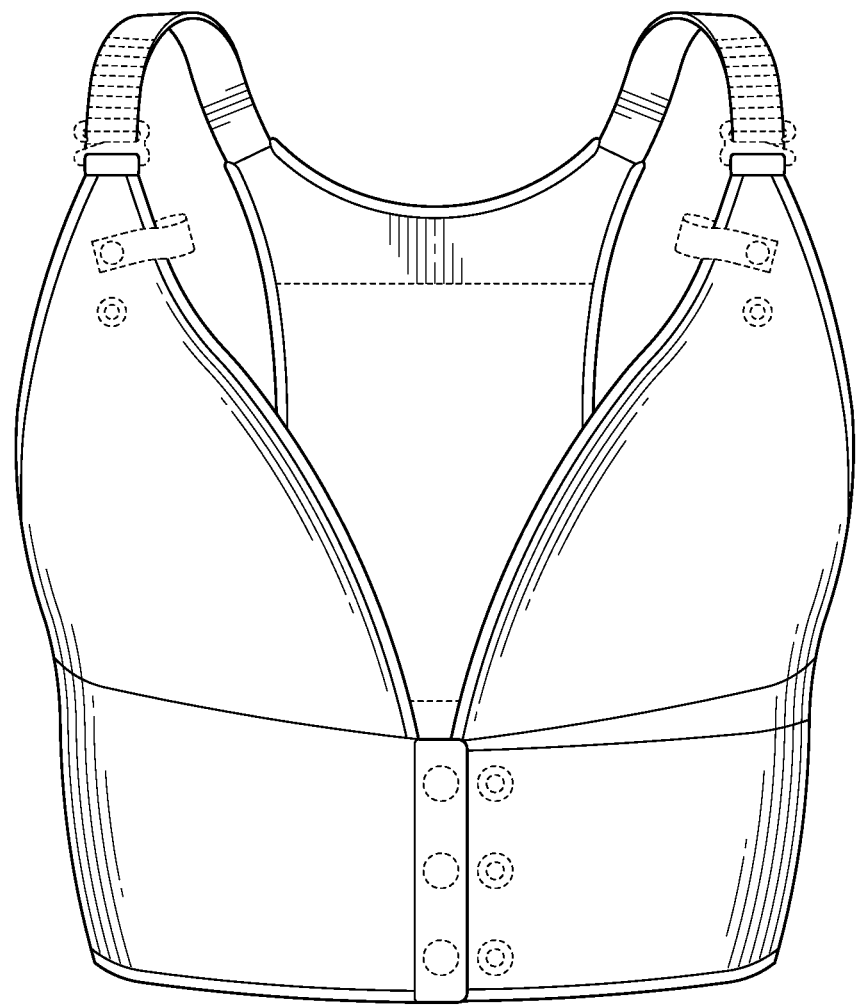
FIG. 16 illustrates the appearance of a front assembled view of the supportive clothing article of FIG. 12.
Figure 17:
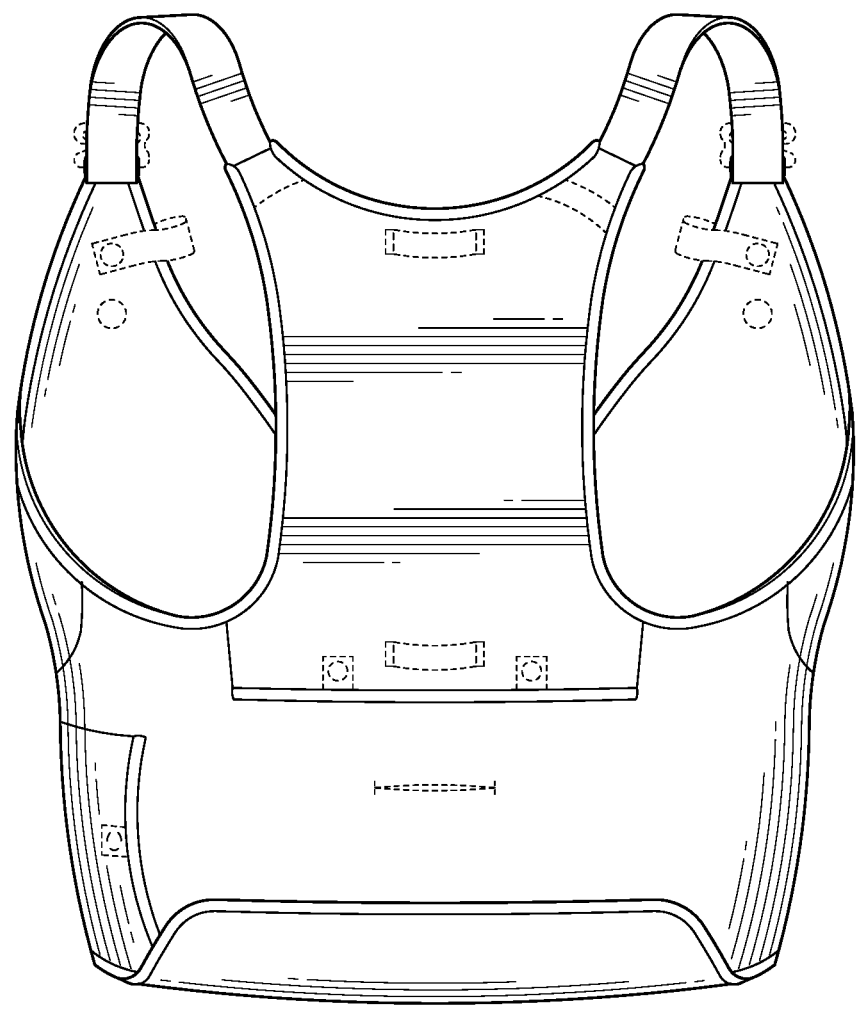
FIG. 17 illustrates the appearance of a rear assembled view of the supportive clothing article of FIG. 12.

The conductive silver mesh 800 in FIG. 8 includes a thin and open structure that allows for gel transmission through the mesh prior to a defibrillation procedure. The conductive silver mesh 800 is not moisture wicking, which keeps some level of body moisture of the patient 302 near the conductive silver mesh 800. Additionally, although not shown in FIGS. 6-8, a gel transmission portion may be provided to transmit gel through the mesh portions of the supportive clothing article 600 prior to any defibrillation.

As seen in FIG. 6, in some embodiments, the supportive clothing article 600 may include a bottom hem 650 allowing access to insert electrodes (not shown) and a flap 652 may be provided to manage the cables from the electrodes. Similar to FIG. 4, a pocket, or receptacle 624 may be provided to receive an electrical component, such as a control module for the defibrillator, and may include electrical contacts. The receptacle 624 may have a plastic interior with electrical contacts to hold the electronic module in place and provide connections to the various other electrical components within the supportive clothing article 600.

The supportive clothing article 600 may also include stabilizer tape (not shown) located between the two fabric layers 500 and 502 within the back portion 626, extending from the top hem 656. The back portion 626 may also include inserted stabilizer tape. The fabric of both the inner layer 500 and outer layer 502 at the top hem 656 may be gathered. The gathered hem 656, as well as the elastic seams, maintain contact between the mesh portion 644 and the back of the patient by pulling in the garment toward the back of the patient. The bottom hem 650 also include a thin strip of polyurethane tape or stabilizer tape to pull the lower edge of the defibrillator electrode(s) against the skin of the patient 302.

Further, a smooth and supportive sateen tape 642 may be provided at the hem under each of the breast support receptacles 612, to provide additional support for the breasts of the patient. In some embodiments, the breast support receptacles 612 and the back portion 626 may include polyurethane tape sandwiched inside the binding at the edges and the seams include a zigzag stitch on the binding. Polyurethane tape 660 may also be included on the inner layer 500 of the belt portion 604 to assist in keeping the belt 604 properly position on the body of the patient during wear, as well as at the upper hem 656.

In some embodiments, wires for the various electrodes that may attach to the belt 304 may be contained between or within the inner fabric layer 500 and the outer fabric layer 502. Such a feature may be used on a clothing supportive article may be the clothing supportive article discussed above, or may be a unisex clothing supportive article that does not contain, for example, breast support receptacles 312.

Similar to FIGS. 3 and 4 discussed above, and as discussed in detail below with reference to FIG. 9, the belt 304 may contain one or more electrodes either attached to, within or on the inner layer 500. For example, slits or pockets 662 may be provided. The electrodes and attached wires may be inserted into receptacle 624 and the electrodes may extend through slits 662 to contact a skin of the patient while the wires connecting the electrodes may remain between in the inner layer 500 and the outer layer 502. In some embodiments, the electrodes and wires may be built into the supportive clothing article and are non-removable. In such embodiments, the belt may be free from pockets or openings to the belt. In some embodiments, the belt 604 may contain electrical contacts for the electrodes to connect, rather than the electrodes themselves, and the wires connecting the electrical contacts are located between the inner layer 500 and the outer layer 502.

All of the features discussed above, with the exception of the breast receptacles 312 and 612, may be provided on a unisex and/or male version of a supportive clothing article for better performance of a unisex and/or male version of the supportive clothing article.

FIG. 9 illustrates a cross-section of a belt portion of a supportive clothing article. Although a belt portion is shown, the cross-section could also apply to the back portion of the supportive clothing article, as well. The supportive clothing article may be any supportive clothing article for a wearable cardioverter defibrillator, such as the supportive clothing article 300 discussed above, as well as a unisex supportive clothing article, also discussed above.

As illustrated in FIG. 9, the supportive clothing article 900 includes an outer layer 902 and an inner layer 904, similar to the outer fabric layer 504 and the inner fabric layer 500 discussed above. Outer layer 902 and inner layer 904 define an interior 906. In some embodiments, the outer layer 902 and the inner layer 904 are stitched together entirely or mostly entirely, such that interior 906 has little to no volume. For example, the outer layer 902 and inner layer 904 may be stitched along the entire hem, except where pockets are provided, such as one of pockets 402, 612, 614, and 706, for example. In FIG. 9, outer layer 902 and inner layer 904 are shown a distance apart for ease of illustration and discussion, and embodiments of the disclosure are not limited to such a distance.

The cross-section view of FIG. 9 illustrates a horizontal cross section through the belt portion of the supportive clothing article 900. The supportive clothing article 900, as mentioned above, may include an electrode 908, which may protrude from the inner layer 904, such as through slit 706 discussed above with reference to FIG. 7. In other embodiments, the inner layer 904 may cover partially or entirely the electrode 908.

The supportive clothing article 900 may also include a receptacle 910 that is recessed from the outer layer 902 and structured to receive an electronics module (not shown) for the defibrillator. The receptacle 910 may be attached to the outer layer 902 or may be removable. The receptacle 910 may be a hard plastic, or other similar material. When the electronics module is not with in the receptacle 910, the supportive clothing article 900 may be washed, etc. The receptacle 910, may correspond, for example, to pocket 402 in the supportive article 300 of FIGS. 4 and 6.

The receptacle 910 includes electrical contacts 912 that electrically connect to electrical contacts on the electronics module. Each of the electrical contacts 912 may be connected to a wire, such as one of wires 914, 916, 918, and 920. Wires 914, 916, 918, 920, and 922 are within the interior 906 of the supportive clothing article 900 and may be connected to the various electrical components 908 and 912. For example, a wire 918 may be connected to one of the electrical contacts 912 and the electrode 908. Then, either an additional wire 922 may continue one from electrode 908, as illustrated in FIG. 9, or the wire 918 may be continuous and contact electrode 908, as well as other electrodes, in lieu of wire 922. The wires 914, 916, 918, and 920 being located within the interior 906 so that a patient 302 does not have to manage the wires and the wires are prevented from getting tangled within a patient's clothing, for example.

FIG. 10 illustrates a top view of the supportive clothing article 900 of FIG. 9. The portions of the supportive clothing article 900 that are viewable are shown in solid lines and the remaining components shown in dashed lines are located within the interior 906 or inner layer 904. As seen in FIG. 10, an outer layer 902 is visible as well as the receptacle 910 and electrical contacts 912. The electrode 908 is also shown in dashed lines since the electrode 908 may either be in the interior 906 or within inner layer 904.

Wires 914-922 may be disposed in a serpentine manner so that wires 914, 916, 918, 920, and 922 may unfold as the fabric layers 902 and 904 stretch when worn by a patient. That is, additional wire is provided within the interior 906 such that when the fabric layers 902 and 904 are not stretched, the wires 914, 916, 918, 920, and 922 are contorted, and when the fabric layers 902 and 904 are stretched, the wires 914, 916, 918, 920, and 922 then straighten out, depending on how far the fabric layers 902 and 904 are stretched. In some embodiments, wires 914-922 may be attached to the insides of either outer layer 902 or inner layer 904, or both, in any manner of way to permit unfolding of the wires 914-922. For example, as seen in FIG. 10, the wires 914, 916, 918, 920, and 922 may be attached to the outer layer 902 by stitching 924 at selected points. In other embodiments, the wires 914, 916, 918, 920, and 922 are not attached to either the outer layer 902 or the inner layer 904.

FIG. 11 illustrate a bottom view of the supportive clothing article 900 of FIG. 9. The portions of the supportive clothing article 900 that are viewable are shown in solid lines and the remaining components shown in dashed lines are located within the interior 906. As seen in FIG. 10, an inner layer 904 is visible as well as the electrode 908. The receptacle 910 and electrical contacts 912 are located on the outer layer 902 and therefore are not visible and are shown in dashed lines. As mentioned above, the wires 914, 916, 918, 920, and 922 are located in the interior 906.

While a single electrode is shown in FIGS. 9-10, as would be understood by one skilled in the art, the belt portion of the supportive clothing article 900 may include multiple electrodes and various wires. Further, the back portion and the belt will include wires that connect the conductive mesh to the electronic module.

FIGS. 12-17 illustrate an appears of a supportive clothing article for a WCD according to an embodiment.

Aspects and examples of the present disclosure operate with various modifications and in alternative forms. Specific aspects have been shown by way of example in the drawings and are described in detail herein below. However, it should be noted that the examples disclosed herein are presented for the purposes of clarity of discussion and are not intended to limit the scope of the general concepts disclosed to the specific examples described herein unless expressly limited. As such, the present disclosure is intended to cover all modifications, equivalents, and alternatives of the described aspects in light of the attached drawings and claims.

References in the specification to embodiment, aspect, example, etc., indicate that the described item may include a particular feature, structure, or characteristic. However, every disclosed aspect may or may not necessarily include that particular feature, structure, or characteristic. Moreover, such phrases are not necessarily referring to the same aspect unless specifically noted. Further, when a particular feature, structure, or characteristic is described regarding a particular aspect, such feature, structure, or characteristic can be employed in connection with another disclosed aspect whether or not such feature is explicitly described in conjunction with such other disclosed aspect.

Examples

Illustrative examples of the technologies disclosed herein are provided below. An embodiment of the technologies may include any one or more, and any combination of, the examples described below.

Example 1 is a supportive clothing article for a wearable cardioverter defibrillator (WCD), comprising a belt, the belt including a first end with a first portion of a fastener and a second end with a second portion of the fastener, wherein the belt is structured to fasten around the torso of patient below the chest area of the patient, the belt including a first conductive mesh portion adjacent the first end of the belt or the second end of the belt; two straps; a back portion extending from the belt at an intermediary position on the belt to each of the two straps, the back portion including a conductive mesh; a first support receptacle attached to and extending from the belt and attachable to one of the two straps; and a second support receptacle attached to and extending from the belt and attachable to the other of the two straps.

Example 2 is the supportive clothing article of example 1, wherein each of the first support receptacle and the second support receptacle are generally triangular shaped.

Example 3 is the supportive clothing article of example 1 or 2, wherein each of the belt, the back portion, the first support receptacle and the second support receptacle have a two fabric layer construction.

Example 4 is the supportive clothing article of example 3, wherein an outer layer of the two fabric layer construction of the belt includes an opening structured to receive an electronic device.

Example 5 is the supportive clothing article of example 4, wherein the opening is located at the intermediary position on the belt.

Example 6 is the supportive clothing article of any one of examples 3-5, wherein the first support receptacle and the second support receptacle each include an opening between an outer layer and an inner layer of the two fabric layer construction, the opening structured to receive a breast support article.

Example 7 is the supportive clothing article of any one of examples 3-6, wherein an outer layer and an inner layer of the two layer fabric construction for the first support receptacle and the second support receptacle are the same type of fabric.

Example 8 is the supportive clothing article of any one of examples 3-7, wherein an outer layer of the two layer fabric construction of the belt and the back portion is a first fabric and an inner layer of the two layer fabric construction of the belt and the back portion is a second fabric different from the first fabric.

Example 9 is the supportive clothing article of any one of examples 1-8, wherein the fastener of the belt includes a snap fastener, a hook and eye fastener, a hook and loop fastener, or a button fastener.

Example 10 is the supportive clothing article any one of examples 1-8, wherein a length of the two straps are adjustable.

Example 11 is the supportive clothing article of example 10, wherein each of the two straps include a plurality of loops, and an end of each of the first support receptacle and the second support receptacle includes a hook structured to attach to one of the plurality of loops to adjust the length of the two straps.

Example 12 is the supportive clothing article of any one of examples 1-11, wherein the first supportive receptacle and the second supportive receptacle each include stabilizer tape at the portion of the respective first and second supportive receptacle that attaches to the belt.

Example 13 is the supportive clothing article of any one of examples 1-12, further comprising a first cable guide attached to an end of the back portion and a second cable guide attached to the end of the back portion.

Example 14 is the supportive clothing article of example 13, wherein the first cable guide and the second cable guide are elastic.

Example 15 is the supportive clothing article of any one of examples 1-14, the belt including a first fabric layer and a second fabric layer, and an interior defined by the first fabric layer and the second fabric layer, the interior including at least one electrical component; and a plurality of wires, at least one wire connected to the at least one electrical component.

Example 16 is the supportive clothing article of any one of examples 1-15, further including polyurethane tape directly above and below the conductive mesh of the back portion.

Example 17 is the supportive clothing article of any one of examples 1-6, further including polyurethane tape along a bottom portion of the belt.

Example 18 is a supportive clothing article for a wearable cardioverter defibrillator (WCD), comprising a belt, having a two fabric layers construction, including a first side with a first portion of a fastener and a second side with a second portion of the fastener, wherein the belt is structured to fasten around the torso of patient below the chest area of the patient, the belt including a first conductive mesh portion on the inner layer adjacent the first side of the belt or the second side of the belt; two adjustable straps; a back portion, having a two fabric layer construction, extending from the belt at an intermediary position on the belt to each of the two straps, an inner layer of the back portion including a conductive mesh; and polyurethane tape attached to an end of the belt.

Example 19 is the supportive clothing article of example 18, wherein an outer layer of the two fabric layers of the belt includes an opening structured to receive an electronic device.

Example 20 is the supportive clothing article of example 19, wherein the opening is located at the intermediary position on the belt.

Example 21 is the supportive clothing article of any one of examples 18-20, wherein an outer layer of the two layer fabric construction of the belt and the back portion is a first fabric and an inner layer of the two layer fabric construction of the belt and the back portion is a second fabric different from the first fabric.

Example 22 is the supportive clothing article of any one of examples 18-21, wherein the fastener of the belt includes a snap fastener, a hook and eye fastener, a hook and loop fastener, or a button fastener.

Example 23 is the supportive clothing article of any one of examples 18-22, wherein a length of the two straps are each adjustable.

Example 24 is the supportive clothing article of example 23, wherein each of the two straps include a plurality of loops, and the proximal end of each of the first support receptacle and the second support receptacle includes a hook structured to attach to one of the plurality of loops to adjust the length of the two straps.

Example 25 is the supportive clothing article of any one of examples 18-24, further comprising a first cable guide attached to a proximal end of the back portion and a second cable guide attached to an end of the back portion.

Example 26 is the supportive clothing article of example 25, wherein the first cable guide and the second cable guide are elastic.

Example 27 is the supportive clothing article of any one of examples 18-26, wherein the back portion includes a gathered hem at a proximal end.

Example 28 is the supportive clothing article of any one of examples 18-27, the belt including a first fabric layer and a second fabric layer, and an interior defined by the first fabric layer and the second fabric layer, the interior including: at least one electrical component; and a plurality of wires, at least one wire connected to the at least one electrical component.

Example 29 is the supportive clothing article of any one of examples 18-28, further including polyurethane tape directly above and below the conductive mesh of the back portion.

Example 30 is the supportive clothing article of any one of examples 18-29, further including polyurethane tape at an end of the belt.

Example 31 is a supportive clothing article for a wearable cardioverter defibrillator (WCD), comprising a patient facing fabric layer; an outer fabric layer; an interior defined by the patient facing fabric layer and the outer fabric layer, the interior including: at least one electrical component; and a plurality of wires, at least one wire connected to the at least one electrical component.

Example 31 is the supportive clothing article of example 31, wherein the electrical component is an electrode.

Example 33 is the supportive clothing article of example 32, wherein the electrode is disposed in the outer fabric layer and is structured to contact skin of a patient.

Example 34 is the supportive clothing article of example 32, wherein the electrode electrically contacts skin of a patient through the outer fabric layer.

Example 35 is the supportive clothing article of any one of examples 31-34, further including a plurality of electrical components.

Example 36 is the supportive clothing article of example 35, wherein the plurality of electrical components includes an electrode and an electrical contact to electrically connect to a removable electronics module.

Example 37 is the supportive clothing article of any one of examples 31-36, wherein the plurality of electrical wires are disposed in the interior in a serpentine fashion.

Example 38 is the supportive clothing article of any one of examples 31-37, wherein the plurality of electrical wires are attached to one of the first layer or the second layer.

The previously described versions of the disclosed subject matter have many advantages that were either described or would be apparent to a person of ordinary skill. Even so, these advantages or features are not required in all versions of the disclosed apparatus, systems, or methods.

Additionally, this written description makes reference to particular features. It is to be understood that the disclosure in this specification includes all possible combinations of those particular features. Where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Although specific examples of the disclosure have been illustrated and described for purposes of illustration, it will be understood that various modifications may be made without departing from the spirit and scope of the disclosure. Accordingly, the disclosure should not be limited except as by the appended claims.

We claim:

1. A supportive clothing article for a wearable cardioverter defibrillator (WCD), comprising:
    a belt, the belt including a first end with a first portion of a fastener and a second end with a second portion of the fastener, wherein the belt is structured to fasten around a torso of a patient below a chest area of the patient, the belt including a first conductive mesh portion adjacent the first end of the belt or the second end of the belt, the belt being configured to receive an electronic component for the WCD;
    two straps;
    a back portion extending from the belt at an intermediary position on the belt to each of the two straps, the back portion including a conductive mesh and at least one cable guide;
    a first support receptacle attached to and extending from the belt and attachable to one of the two straps; and
    a second support receptacle attached to and extending from the belt and attachable to the other of the two straps,
    wherein the supportive clothing article is configured to contain wires that are coupled to the electronic component.

2. The supportive clothing article of claim 1, wherein each of the belt, the back portion, the first support receptacle and the second support receptacle have a two fabric layer construction.

3. The supportive clothing article of claim 2, wherein the first support receptacle and the second support receptacle each include an opening between an outer layer and an inner layer of the two fabric layer construction, the opening structured to receive a breast support article.

4. The supportive clothing article of claim 2, wherein an outer layer and an inner layer of the two layer fabric construction for the first support receptacle and the second support receptacle are the same type of fabric.

5. The supportive clothing article of claim 2, wherein an outer layer of the two layer fabric construction of the belt and the back portion is a first fabric and an inner layer of the two layer fabric construction of the belt and the back portion is a second fabric different from the first fabric.

6. The supportive clothing article of claim 1, wherein a length of the two straps are adjustable.

7. The supportive clothing article of claim 6, wherein each of the two straps include a plurality of loops, and an end of each of the first support receptacle and the second support receptacle includes a hook structured to attach to one of the plurality of loops to adjust the length of the two straps.

8. The supportive clothing article of claim 1, wherein the first supportive receptacle and the second supportive receptacle each include stabilizer tape at the portion of the respective first and second supportive receptacle that attaches to the belt.

9. The supportive clothing article of claim 1, further comprising a first cable guide attached to an end of the back portion and a second cable guide attached to the end of the back portion.

10. The supportive clothing article of claim 1, the belt including a first fabric layer and a second fabric layer, and an interior defined by the first fabric layer and the second fabric layer, the interior including:
    at least one electrical component; and
    a plurality of wires, at least one wire connected to the at least one electrical component.

11. The supportive clothing article of claim 1, further including polyurethane tape along a bottom portion of the belt.

12. A supportive clothing article for a wearable cardioverter defibrillator (WCD), comprising:
    a belt, having a two fabric layers construction, including a first side with a first portion of a fastener and a second side with a second portion of the fastener, wherein the belt is structured to fasten around the torso of patient below the chest area of the patient, the belt including a first conductive mesh portion on an inner layer adjacent the first side of the belt or the second side of the belt, the belt being configured to receive an electronic component;
    two adjustable straps;
    a back portion, having a two fabric layer construction, extending from the belt at an intermediary position on the belt to each of the two straps, an inner layer of the back portion including a conductive mesh and at least one cable guide; and
    polyurethane tape attached to an end of the belt;
    wherein the supportive clothing article is configured to contain wires that are coupled to the electronic component.

13. The supportive clothing article of claim 12, wherein an outer layer of the two fabric layers of the belt includes an opening structured to receive an electronic device.

14. The supportive clothing article of claim 12, wherein an outer layer of the two layer fabric construction of the belt and the back portion is a first fabric and an inner layer of the two layer fabric construction of the belt and the back portion is a second fabric different from the first fabric.

15. The supportive clothing article of claim 12, wherein a length of the two straps are each adjustable.

16. The supportive clothing article of claim 15, further comprising:
a first support receptacle attached to and extending from the belt and attachable to one of the two straps; and
a second support receptacle attached to and extending from the belt and attachable to the other of the two straps
wherein each of the two straps include a plurality of loops, and a proximal end of each of the first support receptacle and the second support receptacle includes a hook structured to attach to one of the plurality of loops to adjust the length of the two straps.

17. The supportive clothing article of claim 12, further comprising a first cable guide attached to a proximal end of the back portion and a second cable guide attached to an end of the back portion.

18. The supportive clothing article of claim 12, the belt including a first fabric layer and a second fabric layer, and an interior defined by the first fabric layer and the second fabric layer, the interior including:
at least one electrical component; and
a plurality of wires, at least one wire connected to the at least one electrical component.

19. A supportive clothing article for a wearable cardioverter defibrillator (WCD), the article having an outside surface and an inside surface, the article comprising:
a back portion;
a belt, the belt extending from the back portion to a first end with a first portion of a fastener and a second end with a second portion of the fastener;
two straps connected to the back portion at a first end;
at least one breast support receptacle attached to and extending from the belt and attachable to at least one of the two straps; and
electrodes adapted to be coupled to the WCD,
wherein the supportive clothing article is configured to maintain the electrodes in proximity to a wearer for operative use by the WCD.

20. The supportive clothing article of claim 19, wherein the at least one breast support receptacle includes:
a first and second breast support receptacle attached to and extending from the belt and attachable to the other of the two straps.

21. The supportive clothing article of claim 19, wherein each of the two straps are adjustable in length.

22. The supportive clothing article of claim 19, further comprising:
at least one pocket configured to receive at least one electrode.

23. The supportive clothing article of claim 19, wherein the at least one breast support receptacle configured to connect to the belt at a front of a patient, the at least one breast support receptacle configured to contact and support at least one breast of the patient.

24. The supportive clothing article of claim 19, wherein the at least one breast support receptacle is coupled to at least one of the two straps by one of loop and hook, a tri glide strap, and elastic straps.

25. The supportive clothing article of claim 19, wherein each of the belt, the back portion, the at least one breast support receptacle have a two-fabric layer construction.

26. The supportive clothing article of claim 25, wherein an outer layer of the two-fabric layer construction of the belt includes an opening structured to receive an electronic device.

27. The supportive clothing article of claim 19, wherein the at least one breast support receptacle are constructed of one or more layers of a thin, stretchable fabric.

* * * * *

UNITED STATES PATENT AND TRADEMARK OFFICE
CERTIFICATE OF CORRECTION

PATENT NO. : 10,926,080 B2  
APPLICATION NO. : 15/889040  
DATED : February 23, 2021  
INVENTOR(S) : L. Gustavson et al.

Page 1 of 1

It is certified that error appears in the above-identified patent and that said Letters Patent is hereby corrected as shown below:

On the Title Page

| Column | Line | |
|---|---|---|
| Abstract | 5 | "of patient" to -- of a patient -- |

In the Claims

| Column | Line | |
|---|---|---|
| 14 | 44 | Claim 12, "of patient" to -- of a patient -- |
| 16 | 33 | Claim 27, "receptacle are" to -- receptacle is -- |

Signed and Sealed this  
Thirteenth Day of July, 2021

Drew Hirshfeld  
*Performing the Functions and Duties of the  
Under Secretary of Commerce for Intellectual Property and  
Director of the United States Patent and Trademark Office*